United States Patent
Wells

(10) Patent No.: US 6,185,468 B1
(45) Date of Patent: Feb. 6, 2001

(54) DECOUPLING CONTROLLER FOR USE WITH A PROCESS HAVING TWO INPUT VARIABLES AND TWO OUTPUT VARIABLES

(75) Inventor: Charles H. Wells, Redwood City, CA (US)

(73) Assignee: Impact Systems, Inc., Los Gatos, CA (US)

(*) Notice: Under 35 U.S.C. 154(b), the term of this patent shall be extended for 0 days.

(21) Appl. No.: 09/026,569

(22) Filed: Feb. 20, 1998

(51) Int. Cl.$^7$ .................................................. G05B 13/02

(52) U.S. Cl. .............................. 700/30; 700/53; 700/72; 162/253; 162/DIG. 10

(58) Field of Search ................................ 700/108, 42, 8, 700/30, 128, 53, 72; 162/253, 252, DIG. 10, DIG. 11

(56) References Cited

U.S. PATENT DOCUMENTS

| | | | |
|---|---|---|---|
| 3,610,899 | * 10/1971 | Dahlin | 702/84 |
| 3,619,360 | * 11/1971 | Persik | 162/258 |
| 3,676,295 | * 7/1972 | Rice | 162/198 |
| 3,847,730 | * 11/1974 | Doering | 162/198 |
| 3,852,578 | * 12/1974 | Rice | 700/30 |
| 4,054,780 | * 10/1977 | Bartley | 700/30 |
| 4,098,641 | * 7/1978 | Casey et al. | 162/198 |
| 5,121,332 | * 6/1992 | Balakrishnan et al. | 700/127 |
| 5,400,247 | * 3/1995 | He | 700/53 |
| 5,400,258 | * 3/1995 | He | 700/129 |
| 5,568,378 | * 10/1996 | Wojsznis | 700/44 |
| 5,791,160 | * 8/1998 | Mandler et al. | 62/611 |
| 5,853,543 | * 12/1998 | Hu et al. | 162/198 |
| 5,944,955 | * 8/1999 | Bossen et al. | 162/198 |

OTHER PUBLICATIONS

Wells, Charles H. "Robust Multivariable IMC Control for Paper Machines." Tappi Journal, Jul. 1999: 140–144.*
Zhang, Weidong and Xiaoming Xu. "Simple Predictor for Processes with Time Delay." Proceedings of the American Control Conference. San Diego, California. Jun. 1999: 822–826.*
Dahlin, E. B. et al. "Designing and Tuning Digital Controllers: Part 1." Instruments and Control Systems. Part 1, Jun. 1968:77–83. Part 2, Jul. 1968:87–91.*
Mahieddine, F. et al. "Decoupling Multivariable Self–Tuning Controller for Varying Time Delays." IEE Proceedings. Part D, Control Theory and Applications v. 134 (Sep. '89) pp. 209–14.*
Heaven, M. et al. "Applications of Model–Based Tuning and Analysis Tools to Paper Machine Control." Pulp and Paper Canada, vol. 98, No. 7, Jul. 1997, pp. 54–48.*
Morari, M. and Zafirious, E., "Robust Process Control." Englewood Cliffs, 1989, pp. 393–428.*

(List continued on next page.)

*Primary Examiner*—William Grant
*Assistant Examiner*—Edward F. Gain
(74) *Attorney, Agent, or Firm*—Jerry G. Wright; Flehr Hohbach Test Albritton & Herbert LLP

(57) ABSTRACT

A decoupling controller for use with a process such as paper-making having two input variables such as stock flow and steam pressure and two output variables such as moisture and basis weight. Decoupling is accomplished by the use of linked internal model controllers where for each individual unit of the linked pairs, a P.I.D. (proportional, integral, derivative) unit includes all of the feedback loop gains and then the process itself is modeled by a first order transfer function and deadtime units with two cross-linked error signals fed back. A specific technique of cross-linking the internal model controllers eliminates cross-coupling between the input and output variables.

9 Claims, 6 Drawing Sheets

OTHER PUBLICATIONS

Bahill, A. Terry. "A Simple Adaptive Smith–Predictor for Controlling Time–Delay Systems." Control Systems Magazine. vol. 3. May, 1983, 16–22.*

Dumont, Guy A. "System Identification and Adaptive Control in Papermaking." Fundamentals of Papermaking: Transactions of the Ninth Fundamental Research Symposium Head at Campridge: Sep. 1989. Mechanical Engineering Publication Limited, London.*

* cited by examiner

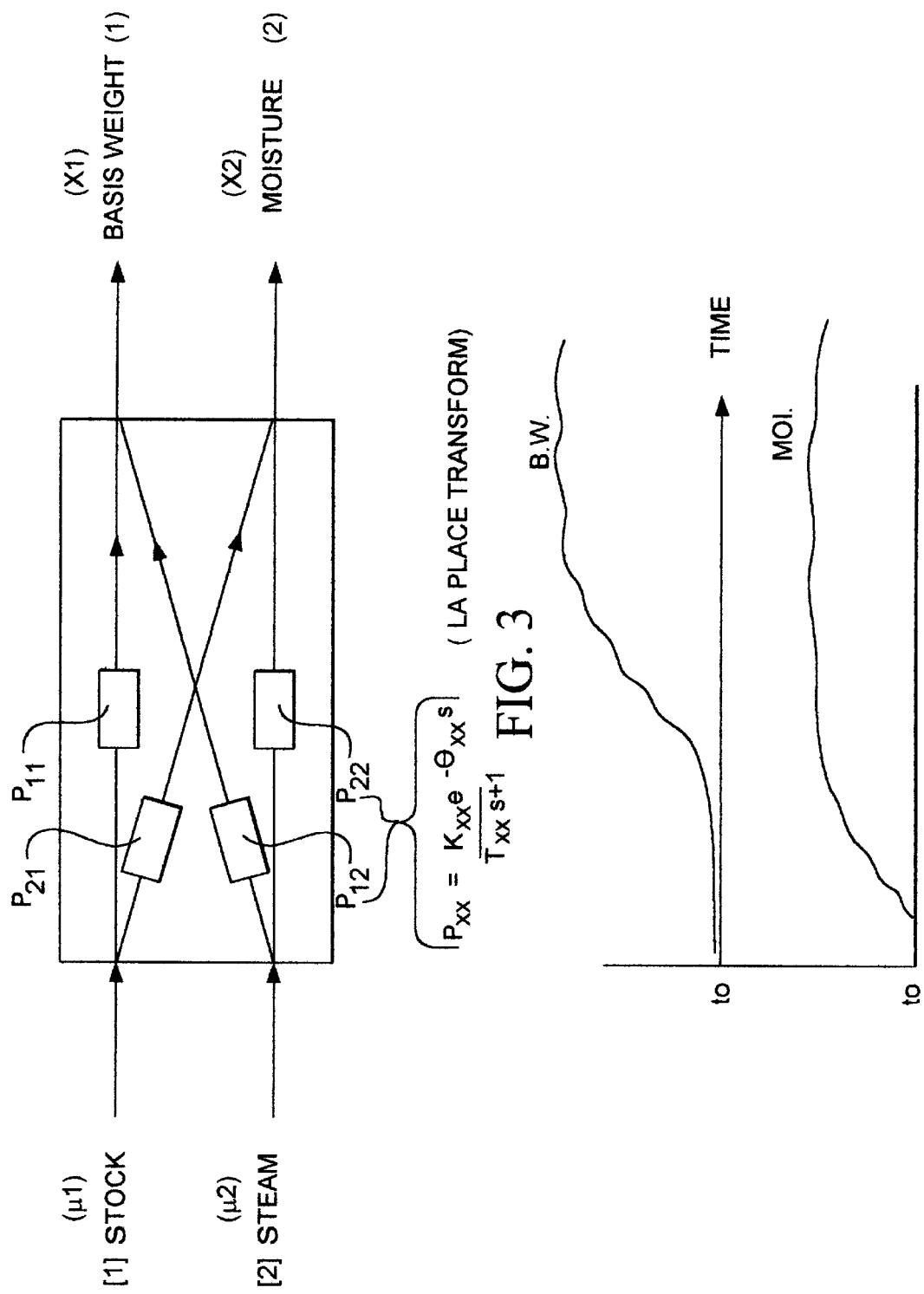

DECOUPLING CONTROLLER FOR USE WITH A PROCESS HAVING TWO INPUT VARIABLES AND TWO OUTPUT VARIABLES

INTRODUCTION

The present invention is directed to a decoupling controller for use with a process having two input variables and two output variables and, more specifically, to a paper-making process where the input variables are dry stock flow and steam pressure to a dryer section and the output variables are basis weight and moisture.

BACKGROUND

In the paper-making process, the process itself has long deadtimes relative to the process time constant. This makes control difficult. There are typically two unique deadtimes; one is for the time required for a change in basis weight when the input variable, stock flow, is changed and the other is the time for variation in steam to affect the final moisture carried by the paper sheet. A further difficulty in the paper-making process is the cross-coupling affect; that is, each input variable affects both output variables. Hence, a decoupling controller is desired to regulate the outputs independently; for example, the operator would like to change the setpoint of the basis weight controller without changing the value of the moisture.

Two rather crude techniques have been utilized for decoupling. In a first, a setpoint is changed only once every five minutes, for example, for changes in stock flow and once every minute for changes in steam. This is a much longer period of time than the generation of output data by a sensor which scans across the width of the paper, for example, every 20 seconds.

A second proposed decoupling technique is to provide absolute decoupling constants between changes in stock flow and steam pressure. These might be termed "compensating changes". However, these are mere guesses and do not compensate for grade changes or speed changes and do not take into account that the coupling effect may be nonlinear. One other problem with a controller for a paper-making machine discussed above, is the fact that the measurements of outputs occur either at long intervals or can occur asynchronously due to sheet breaks or standardization. In any case, scan measurements (which may take up to 120 seconds) only occur every 20 seconds at best.

OBJECT AND SUMMARY OF INVENTION

A general object of the present invention is to provide an improved decoupling controller for use with a process having two input variables and two output variables.

In accordance with the above object, there is provided a decoupling controller for use with a process having two input variables U1, U2 and two output variables X1, X2 where in the process each input variable affects both output variables (that is they are coupled), such process having desired setpoints S1, S2 for the output variables. Such decoupling controller comprising two pairs of linked internal model controllers, each internal model controller (IMC) including a proportional, integral, derivative (P.I.D.) velocity unit C11, C21, C12, and C22 for respectively receiving from a first pair of difference junctions total process error, et1, et2, in a feedback loop for the process and producing said input variables U1, U2, which are control inputs to the process itself, such P.I.D. units taking into account loop, proportional, integral and derivative gains of the feedback loop for both direct and cross-coupling.

Four first order transfer function units K11, K12, K21, and K22 receive as inputs U1, U2, the K11, K22 units providing predicted values of X1, X2, the K21, K12 units providing predicted outputs of X1, X2 due to cross-coupling.

Means feed back to a pair of second summing junctions the outputs of K11, K12 and K22, K21 respectively.

Means couple the outputs of the second summing junctions, which are total predicted values of X1 and X2 taking into account cross-coupling, to a pair of third summing junctions, which also receive modeling error signals representing the difference between the actual X1 and X2 values and estimated values Y1 and Y2, from a pair of fifth junctions.

Means feed the summed output of the third pair of summing junctions to the first pair of difference junctions, which have as the other difference input the setpoints S1, S2 to provide the total process error inputs et1 and et2 to C11, C21 and C12, C22;

Means take the deadtime of the process into account (that is the lag time between the change of input variables and output variables), including four deadtime units, D11, D21, and D12, D22, having their inputs respectively connected to the outputs of K11, K21, K12, and K22, including a pair of fourth summing junctions having as outputs the current estimated values Y1, Y2 of the X1, X2 output variables, where one of the pair of fourth summing junctions, sums the outputs of D11, D12 and the other of the pair of summing junctions, sums the outputs of D22, D21.

Means couple the outputs of the fourth pair of summing junctions, to the fifth pair of difference junctions to take the difference between the actual outputs X1, X2 and the estimated values Y1, Y2, such differences being the modeling error signals.

Means feed back the modeling error signals to the third pair of summing junctions.

BRIEF DESCRIPTION OF THE DRAWINGS

FIG. 3 is a schematic representation of the four transfer functions involved in the present paper-making process.

FIG. 4 shows characteristic curves useful in understanding the present invention.

DETAILED DESCRIPTION OF PREFERRED EMBODIMENT

Figure 1:
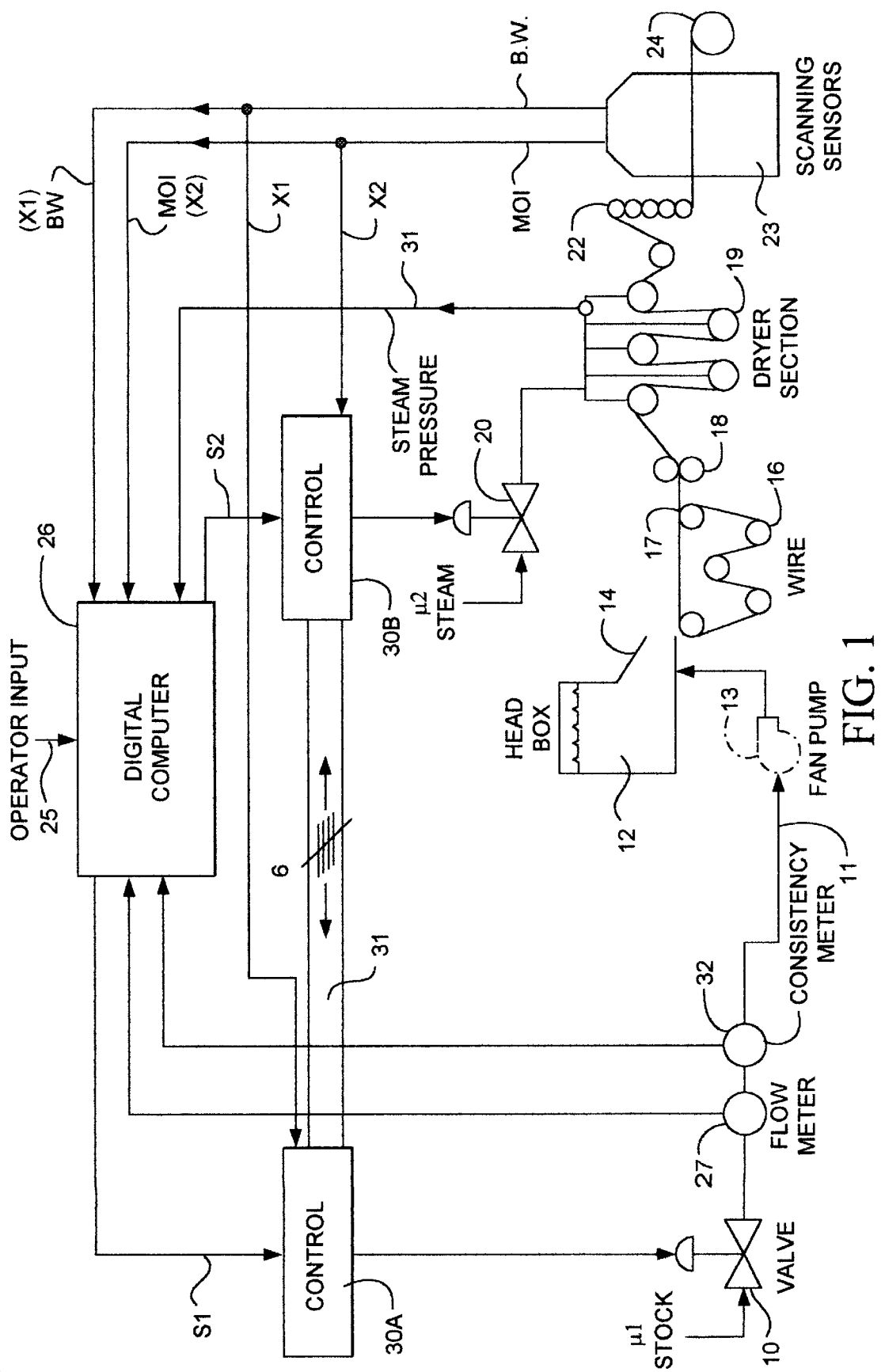
FIG. 1 is a simplified block diagram of a paper-making machine, including the associated control hardware and software embodying the present invention.

FIG. 1 illustrates a typical paper-making machine, which includes an associated control hardware and software configuration as used in the present invention. Raw paper stock is supplied to the machine via a stock valve 10 and a stock line 11 to a head box 12 by a fan pump 13. The pump and water mixture jets from head box 12 through a slice 14 on top of and parallel to wire 16. This forms a wet web 17, which on leaving wire 16 passes through rollers 18, which remove much of the water from the web and essentially converts it to a sheet of wet paper. Thereafter, the paper sheet passes through a dryer section 19 consisting of several rollers to which steam is supplied by steam control valve 20. Steam heats the rollers and, consequently, evaporates much of the water in the paper sheet so that the paper emerging from the dryer section 19 has the desired moisture content (MOI). Thereafter, the paper passes through a calendar stack 22 through scanning sensors 23 and is wound on the reel 24.

Scanning sensors 23 scan across the width of the paper approximately every 20 seconds and provide a measurement of the output variables of basis weight (B.W.) and moisture (MOI). In the present invention, either basis weight, dry weight, or conditioned weight may be used; the latter is preferred. Conditioned weight is from a practical standpoint, dry weight where a standard 8 percent moisture factor is added. The two output variables from the scanning sensors 23 are also designated X1 and X2. The scanned moisture and basis weight values are coupled to the digital computer 26 for processing along with an operator input 25. Typically, in the cross direction of the paper, 240 measurements are made and these are averaged to provide a single "end of scan" measurement. This is therefore one of the measurements made in the machine direction. Both basis weight and moisture (X1 and X2) are also connected to control units 30A and 30B in a manner which will be illustrated in FIG. 2. The two control units are actually part of a single interlinked decoupling controller embodying the present invention as indicated by the 6-wire interface 31. Controller portion 30A has as inputs a setpoint S1 from the digital computer 26 and X1 and as an output, the control value U1, which drives the stock valve 10 to provide a dry stock (fiber) flow rate of U1. Similarly, controller portion 30B receives the setpoint S2 (actually, the steam pressure) from digital computer 26 along with X2 and by its output U2 drives the steam valve 20 to provide a U2 steam input.

Digital computer 26 has as other feedbacks the steam pressure line 31 from dryer section 19 and also flow meter 27 and a consistency meter 32, which determine the pounds per minute of dry stock flow.

Figure 2:
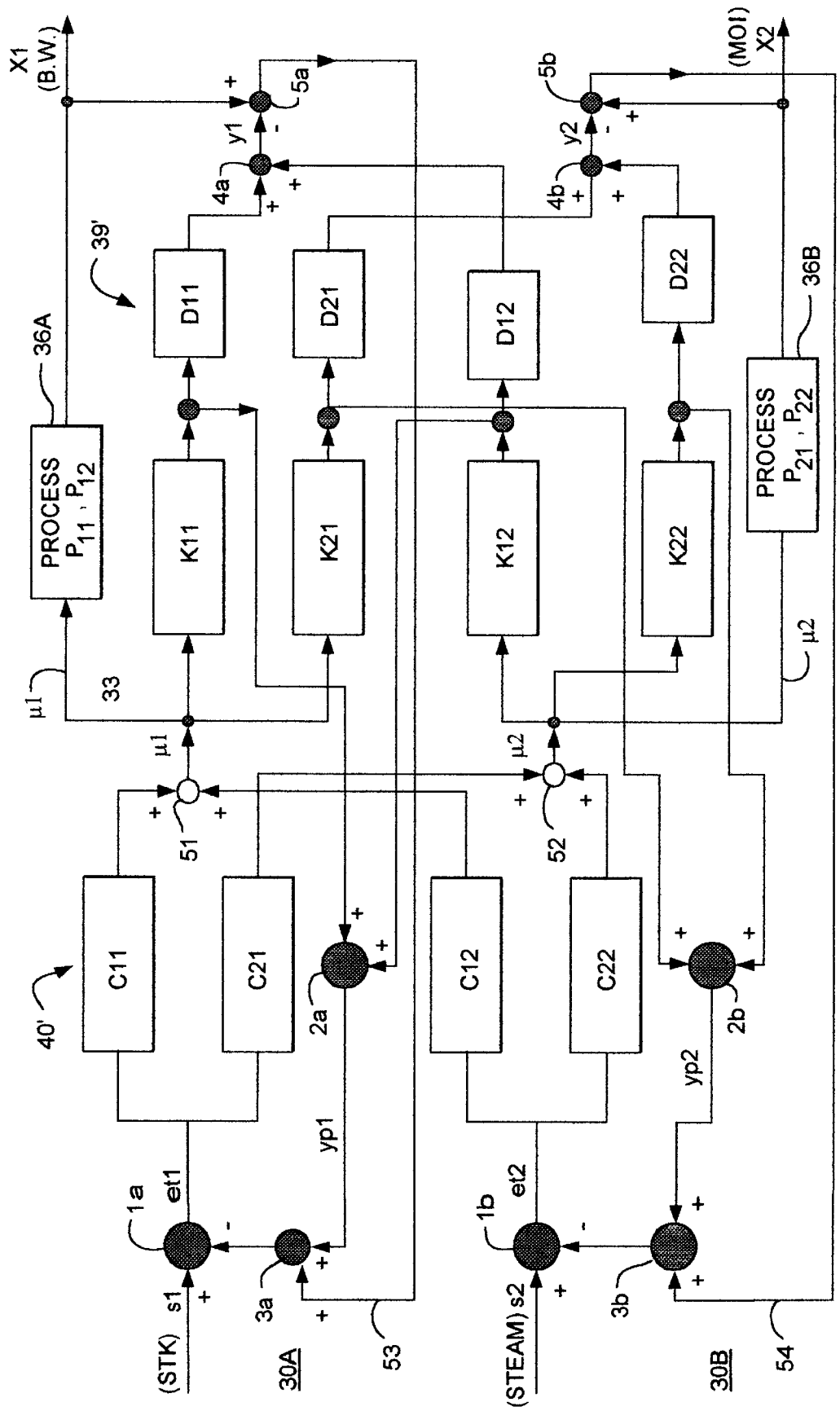
FIG. 2 is a detailed schematic block diagram of the control units of FIG. 1.

Referring to FIG. 2, the decoupling controller portions 30A and 30B are shown in greater detail and especially how they are interlinked. The paper-making process, fully illustrated in FIG. 1 is shown twice, both at 36A and 36B, as being driven by the input variables U1 (stock flow) and U2 (steam) and having the outputs X1 (basis weight) and X2 (moisture).

The real process, illustrated in FIG. 3, is represented by four unknown transfer functions $P_{11}$, $P_{12}$, $P_{21}$, and $P_{22}$. The P-type functions, with the 11 and 22 subscripts represent the direct transfer functions of stock to basis weight and steam to moisture; the other cross-coupling subscripts 21 and 12, relate to how moisture is affected by changing stock and how basis weight is affected by a change in steam. The P functions can be represented by the associated Laplace Transform where the theta superscript is a deadtime function or delay function and the remainder is a time constant and gain, or rather a first order transfer function K.

FIG. 4 illustrates the delay or deadtime of the process. Assuming a time, $t_o$, when a change is made for stock, there is a delay until basis weight reaches a constant value; and the same is true for the change in steam for moisture. In the background of the invention, prior attempts at decoupling were discussed.

Figure 5:
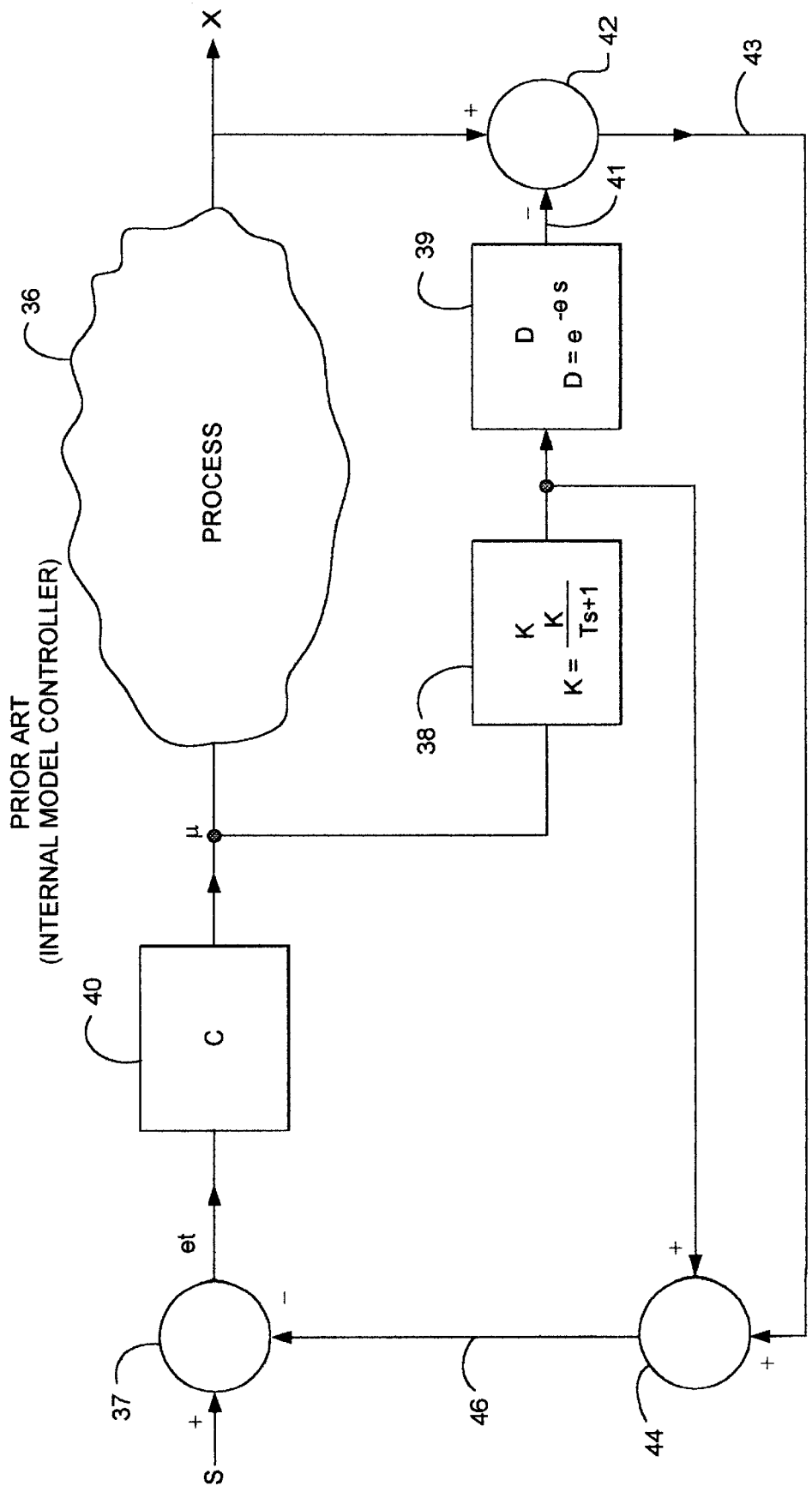
FIG. 5 is a schematic block diagram of a prior art controller as utilized in the present invention.

With regard to the present invention and referring to FIG. 5, it has been found that when a prior art type internal model controller (IMC), as shown in FIG. 5, for a single loop only and for synchronous measurements in time, is adapted to a multi-variable system, it will accommodate deadtime, asynchronous behavior, and when two pairs of IMC's are linked, as is illustrated in FIG. 2, provide very effective decoupling. However, first referring to FIG. 5, to serve as a background for the total decoupling controller of FIG. 2, the internal model controller has a setpoint input S and a process at 36 and an output variable X. A difference junction 37 provides a total error signal, et, to a controller C, 40, which then provides an input control signal U to the process 36. This input control signal, however, also drives a simulated model of process 36, which is characterized by the Laplace Transform (see FIG. 3) of a K function 38 and a D function 39 as illustrated by the accompanying formulas. This process model provides an estimated X value at 41, which at the difference junction 42 is compared to the actual X value to generate a feedback error signal on line 43. However, this error signal is not coupled back to the input until it is summed at a junction 44 with the raw output of the K model 38 (that is before a deadtime is taken into account). Then on line 46 and junction 37, a difference is taken with the setpoint, S, to provide the total error, et. The unit 40 is actually a proportional, integral, derivative (P.I.D.) type controller which is illustrated by the following equation which produces an output U in response to a total error input, et:

$$C = \frac{u(s)}{e_t(s)} = K_L(K_P + K_I/s + K_d s)$$

Its constants are:
$K_L$=loop gain
$K_P$=proportional gain (generally approx. less 1)
$K_I$/s=integral gain (this is an acceleration factor which is about 0.5) and s is the Laplace operator.
$K_d s = K_d$ is derivative gain which is in the range of 0.3 to 0.8 and s is the Laplace operator.

Thus, in summary the internal model controller models the process 36 by the use of the first order transfer function K (unit 38) with a deadtime D (unit 39). In general, this internal model controller (IMC) is for a single loop only and not for asynchronous use. For use in the chemical industry see the book entitled, "Robust Control" by Manfred Morari and Evanghulos Zafiriou, Prentice-Hall, 1989. It is quite apparent, from examination of FIG. 5, if there is a deadtime equal to 0, that is D=0, then it becomes a standard proportional integral derivative (P.I.D.) controller. The loop gain, $K_L$ is not normally part of a standard IMC. In the present invention, it has been discovered that if $K_L$ is made the reciprocal of the model gain, K (unit 38), the above equation becomes non-dimensional to allow the loop to be easily pre-tuned. The value of the constants are believed ideal to pretune for a typical paper making machine. They were derived by trial and error.

Referring back to FIG. 2, this illustrates the decoupling controller of the present invention, which in effect incorporates four internal model controllers which are linked together. The C-type unit 40 of FIG. 5, designated 40', has two pairs of linked P.I.D. units C11, C21, C12, and C22. The numerical designations, of course, conform to the transfer functions illustrated in FIG. 3. Thus, C11 and C22 are the direct model of the process change for driving U1 and U2, respectively, and then for the other two, C21 relates to S1, X2, and C12 to S2, X1. In other words, these P.I.D. units are cross-coupled to produce at the additive junctions 51 and 52, the U1 and U2 control values to the process 36A, 36B. In order to provide fast response, the units 40' are of the P.I.D. velocity type to eliminate "reset windup".

"Reset Windup" occurs in a feedback control system which integrates error. But when the system variable is constrained at a 100% value (and thus the setpoint cannot be achieved) an intolerable error is built up by integration. This cannot happen with the present P.I.D. unit since the term, "$K_p e_t$", has no integral. The operation of units 40' is determined by the following equation which, of course is a form of its basic equation given above:

$$sC(s)=sU(s)=K_L(K_P s+K_I+K_d s^2)e_t(s)$$

or in time domain;

$$\delta U = K_L\left(K_P \frac{\delta e_t}{\delta t} \cdot \delta t + K_I e_t + K_d \frac{\delta^2 e_t}{\delta t^2} \cdot \delta t\right)$$

(where $\delta$ is the difference operator)

As discussed in combination with FIG. 5, the units 40' take into account loop gain, proportional gain, integral gain, and derivative gains involved in the feedback loops illustrated in FIG. 2.

Next, the K11, K21, and K12, K22 units, also designated 38', receive as respective inputs U1, U2. The K12 and K21 units provide predicted outputs of X1, X2 due to cross-coupling. These outputs, in manner somewhat similar to FIG. 5, are cross-coupled back to junctions 2a and 2b and summed with the K11 and K22 outputs. Thus, the output of the second summing injunction pair, 2a and 2b, is actually the total predicted value of X1 and X2 (taking into account cross-coupling, but without deadtime). These are designated yp1 and yp2. These outputs of the 2a and 2b junctions are then connected to a third pair of junctions, 3a and 3b, which also receive on the lines 53 and 54 modeling error signals representing the difference between the actual X1 and X2 values and the estimated values, Y1 and Y2. Finally, the outputs of the junctions 3a and 3d are fed back to the first pair of difference junctions 1a and 1b to provide the total process error, et1 and et2.

Deadtime is taken in account by the D units 39' which receive the outputs of the respective K units. The deadtime is, of course, the lag time between the change of input variables and output variables. The deadtime units D11, D21 and D12, D22 have their inputs respectively connected to the outputs of K11, K21 and K12, K22. A current estimate Y1, Y2 of the X1 and X2 output variables is provided at the summing junctions 4a and 4b; junction 4a sums D11 and the cross-coupled D12 and junction 4b sums D22 and the cross-coupled D21.

And then lastly, the junctions 5a, 5b take the difference between the actual outputs X1 and X2 and the estimated values Y1 and Y2 to provide the modeling error signal on lines 53 and 54.

Thus, in a robust and elegant manner, the internal model controller of FIG. 5 has been converted by the specific interlinking as shown in FIG. 2 to compensate for deadtime and provide for instant response to setpoint changes and at the same time to effectively decouple weight from moisture.

To estimate values for the K and D units, 38' and 39', bump tests are used along with the knowledge and experience of an operator of the process.

The above process model with four transfer functions also accommodates use in a wide variety of processes in addition to paper machines, such as in the petrochemical, mining, waste water treatment and food processing industries.

Typically, in these cases, the gas or liquid stream is sampled isokinetically with the sample drawn to a chemical analyzer, such as a gas or liquid chromatograph resulting in a time lag.

In order to execute the above equations asynchronously, the differential equations are solved analytically. For example:

$$\frac{x}{u}(s) = \frac{K}{Ts+1} \text{ in Laplace is}$$

$$\frac{dx}{dt} = -\frac{1}{T}x + Ku \text{ in time.}$$

Solving for x, given u=constant over a short period.

$$x(t) = e^{-\frac{t}{T}}x(t_o) + \left(1 - e^{-\frac{t}{T}}\right)Ku \quad (1)$$

So, given the measurement at $t=t_o$; $x(t_o)$; the future values of x can be computed using Eq.(1) as long as u is constant beginning at $t_o$. To find yp(t), simply delay x(t) by the time delay. Thus, the foregoing demonstrates how to execute the equations asynchronously.

Executing the controller at random intervals is ideal for paper machine control systems since the end of scan measurements are at random times. Also, since the P.I.D. unit 40' is of the velocity form, no movement of the inputs to the process are possible between scan intervals. The controller does not have to be programmed explicitly to handle scanner standardizations or sheet breaks.

The P.I.D. units 40' are preferably implemented in the velocity mode to eliminate "reset wind-up". However, depending on the process other type modes might be used.

Figure 6:
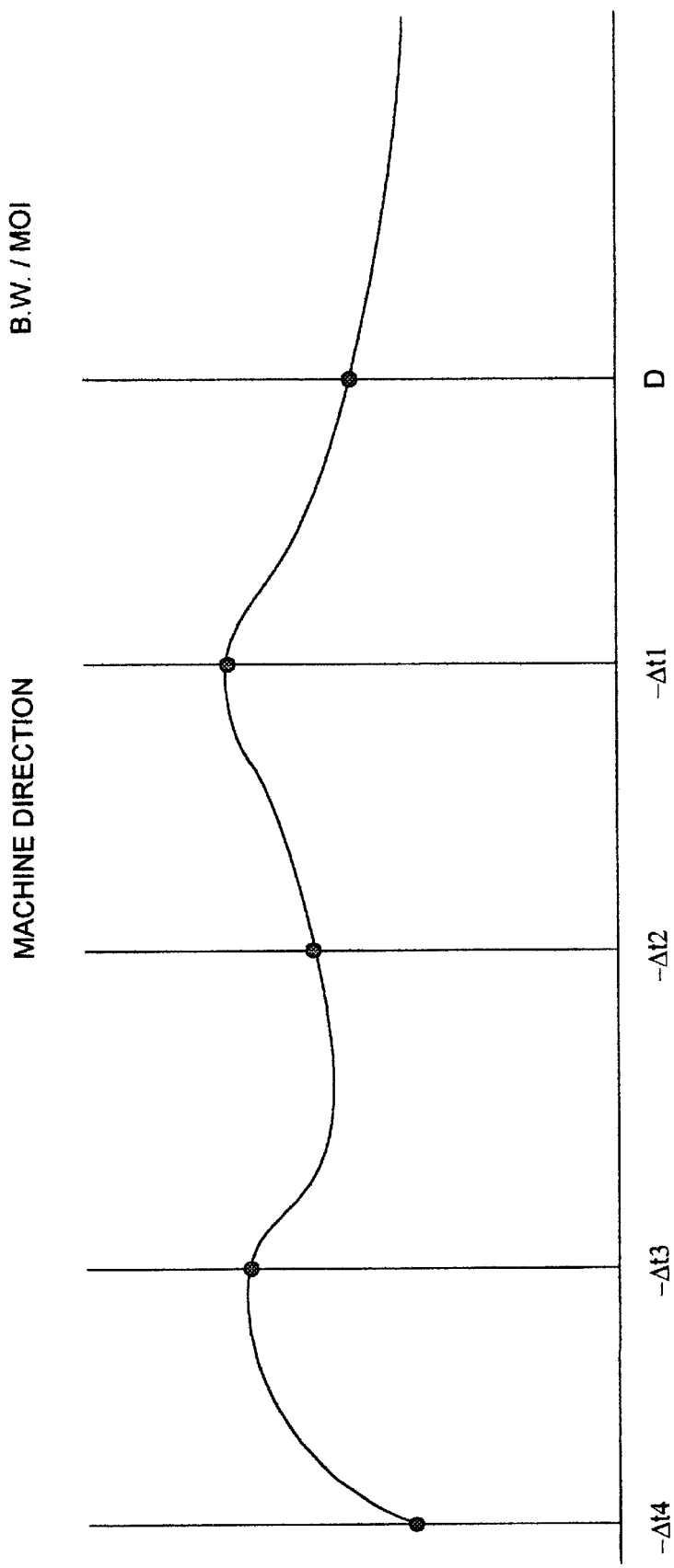
FIG. 6 is a scan data output characteristic useful in understanding the present invention.

FIG. 6 illustrates typical data received in the machine direction of either basis weight or moisture. Five data points are illustrated. The use of a sliding least squares method of polynomial filters provides a single best estimated value of X1 or X2, as well as dx/dt and $dx^2/dt^2$ which, of course, relate to velocity and acceleration.

In order to provide a well-tuned feedback system, the loop gain, $K_L$, (see FIG. 5) of the controller units 40' is set as the inverse of the related K functions of the K11, K12, K21, and K22 modeling units.

Figure 7:
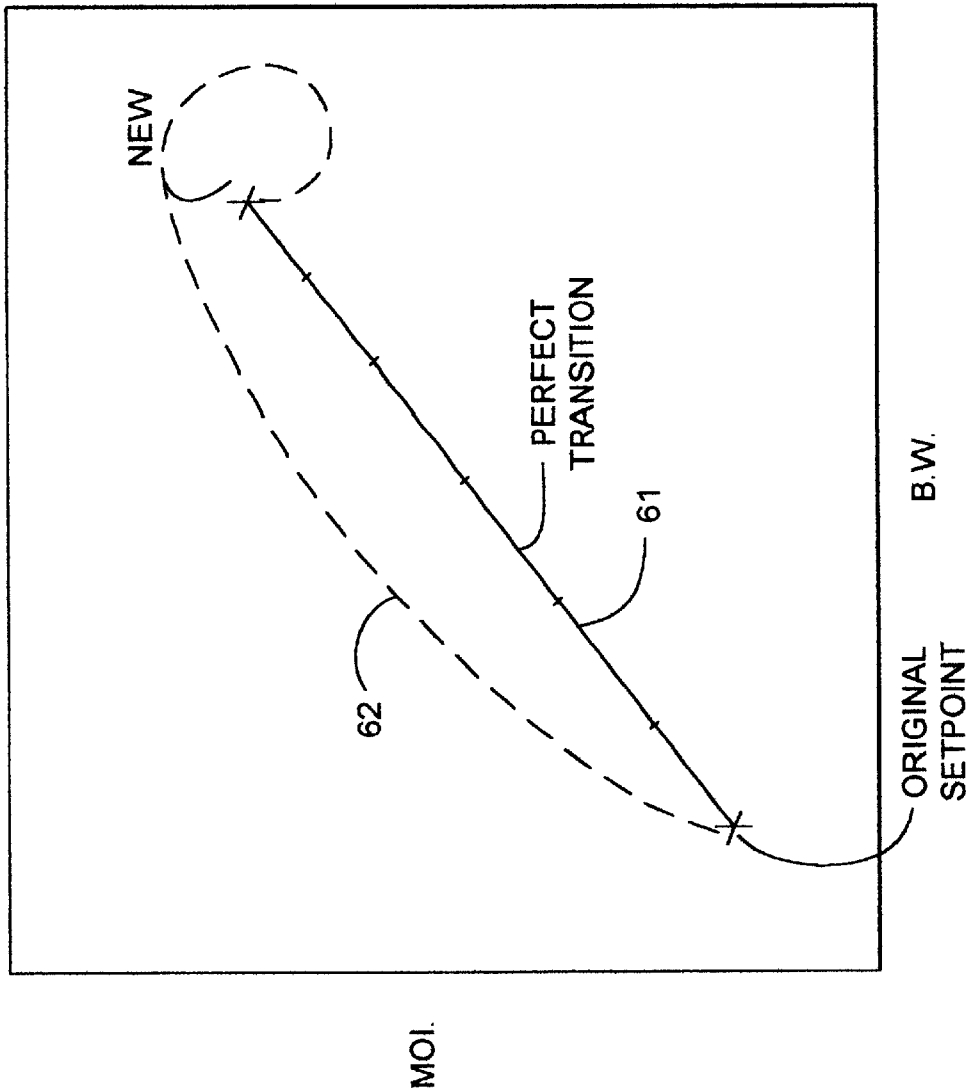
FIG. 7 is a phase planes chart used in the present invention.

In addition, the K11 first order transfer function is adjusted for an increase in the paper machines' speed (or trim). Here, with a speed increase the loop gain, $K_L$, of the P.I.D. is decreased since it is the inverse of K11. This is computed by the following fiber balance equation:

$$D_{1n}*K_{11}=D_w*S*t$$

where $D_{1n}$—input fiber rate, g/sec, $D_w$—output dry weight scan average, g/m$^2$, $K_{11}$—process gain, S—speed of paper, m/min, t—trim of paper, m FIG. 7 shows a method of displaying the two dependent variables such as basis weight and moisture. In the case of a paper machine, the display includes the last 20 values of weight and moisture displayed on an XY chart with connecting lines between the data points. The chart is known as a phase planes chart in control theory and is used to analyze regions of stability and performance under transient conditions. Thus, as shown by the straight line 61, this is a perfect transition between an original setpoint and a new setpoint. However, the dashed line 62 illustrates a somewhat imperfect transition which, however, presents to the operator a possibility of improving by tuning the feedback system, the transition.

Thus, an improved decoupling controller for use with a process having two input variables and two output variables has been provided.

What is claimed is:

1. A decoupling controller for use with a paper making machine process having two input variables (U1 and U2) which are dry stock flow and steam pressure and two output variables (X1 and X2) which are basis weight and moisture where in the process each input variable affects both output variables, such process having desired setpoints (S1, S2) for said output variables such decoupling controller comprising:

linked internal model controller means including two pairs of proportional, integral, derivative P.I.D. velocity units (C11, C21; and C12, C22) each pair respectively receiving from a first pair of difference junctions total process error, (et1, et2) in a feedback loop for the process and producing said inputs (U1, U2), which are control inputs to the process itself, such P.I.D. units taking into account loop, proportional, integral, and derivative gains of the feedback loop for both direct and cross-coupling;

four first order transfer function units (K11, K12, K21, and K22) for receiving as inputs U1, U2, said K11, K22 units providing predicted values of X1, X2, said K21, K12 units providing predicted outputs of X1, X2 due to cross-coupling;

means for feeding back to a pair of second summing junctions the outputs of K11, K12 and K22, K21 respectively;

means for coupling the outputs of said second summing junctions, which are total predicted values of X1 and X2 taking into account cross-coupling, to a pair of third summing junctions;

means for feeding the summed output of said third pair of summing junctions to said first pair of difference junctions, which have as the other difference input the setpoints S1, S2 to provide said total process error inputs et1 and et2 to C11, C21 and C12, C22, respectively;

means for taking the deadtime of said process into account which is the lag time between the change of input variables and output variables, including four deadtime units, (D11, D21, and D12, D22), having their inputs respectively connected to the outputs of K11, K21, K12, and K22, including a pair of fourth summing junctions having as outputs current estimated values (Y1, Y2) of the X1, X2 output variables where one of the pair of fourth summing junctions, sums the outputs of D11, D12 and the other of the pair of summing junctions, sums the outputs of D22, D21;

means for coupling the outputs of said fourth pair of summing junctions, to a fifth pair of difference junctions to take the difference between the actual outputs X1, X2 and the estimated values Y1, Y2, such differences being modeling error output signals;

means for feeding back said modeling error output signals to said third pair of summing junctions;

and where said K11 the process gain for stock, is increased for an increase in the paper machine speed and said feed back loop gain of the correspondin a P.I.D. unit, C11, is decreased.

2. A decoupling controller as in claim 1 where measurement of said output variables is done asynchronously.

3. A decoupling controller as in claim 2 where a plurality of said measurements are made over said paper in a machine direction and including polynomial filtering means for such measurements to produce a best estimate of value.

4. A decoupling controller as in claim 3 where said paper is scanned in a cross-direction to provide a plurality of measurements of X1, X2 including means for averaging to provide an end of scan measurement which constitutes one of said plurality of measurements in such machine direction.

5. A decoupling controller as in claim 4 where said polynomial filtering also provides first and second derivatives proportional to velocity and acceleration.

6. A decoupling controller as in claim 1 where said loop gain of said internal model controllers is the inverse of corresponding a K11, K12, K21, and K22 units.

7. A decoupling controller as in claim 1 where said process gain change K11 is computed in the following fiber balance equation:

$$D_{1n} * K_{11} = D_W * S * t$$

where
   $D_{1n}$—input fiber rate
   $D_W$—output fiber rate
   $K_{11}$—process gain
   S—speed of paper
   t—trim of paper.

8. A decoupling controller as in claim 1 where bump tests are used to estimate gains for said K and D units.

9. A decoupling controller as in claim 1 including means for plotting a phase planes chart using said basis weight and moisture outputs as graph ordinates.

* * * * *